(12) United States Patent
Angulo Gonzalez

(10) Patent No.: US 11,534,433 B2
(45) Date of Patent: Dec. 27, 2022

(54) ANTIFUNGAL AGENTS WITH ENHANCED ACTIVITY IN ACIDIC PH

(71) Applicant: Scynexis, Inc., Jersey City, NJ (US)

(72) Inventor: David A. Angulo Gonzalez, Palmetto Bay, FL (US)

(73) Assignee: Scynexis, Inc., Jersey City, NJ (US)

( * ) Notice: Subject to any disclaimer, the term of this patent is extended or adjusted under 35 U.S.C. 154(b) by 314 days.

(21) Appl. No.: 16/636,230

(22) PCT Filed: Jul. 31, 2018

(86) PCT No.: PCT/US2018/044619
§ 371 (c)(1),
(2) Date: Feb. 3, 2020

(87) PCT Pub. No.: WO2019/028034
PCT Pub. Date: Feb. 7, 2019

(65) Prior Publication Data
US 2020/0390751 A1 Dec. 17, 2020

Related U.S. Application Data

(60) Provisional application No. 62/541,370, filed on Aug. 4, 2017.

(51) Int. Cl.
| | | |
|---|---|---|
| *A61K 31/4409* | (2006.01) | |
| *A61P 15/02* | (2006.01) | |
| *A61P 31/10* | (2006.01) | |
| *A61K 9/00* | (2006.01) | |

(52) U.S. Cl.
CPC ........ *A61K 31/4409* (2013.01); *A61K 9/0014* (2013.01); *A61K 9/0053* (2013.01); *A61P 15/02* (2018.01); *A61P 31/10* (2018.01)

(58) Field of Classification Search
CPC .............. A61K 31/4409; A61K 9/0014; A61K 9/0053; A61P 15/02; A61P 31/10
See application file for complete search history.

(56) References Cited

U.S. PATENT DOCUMENTS

| | | |
|---|---|---|
| 5,756,472 A | 5/1998 | Liesch et al. |
| 8,188,085 B2 | 5/2012 | Greenlee et al. |
| 2016/0207956 A1 | 7/2016 | Zhang |

FOREIGN PATENT DOCUMENTS

| | | |
|---|---|---|
| WO | WO-2007/126900 A2 | 11/2007 |
| WO | WO-2007/127012 A1 | 11/2007 |
| WO | WO 2010/019203 A1 | 2/2010 |
| WO | WO-2016/118396 A1 | 7/2016 |

OTHER PUBLICATIONS

Boikov et al., "In vitro activity of the novel echinocandin CD101 at pH 7 and 4 against *Candida* spp. isolates from patients with vulvovaginal candidiasis," J Antimicrob Chemother 2017; 72: 1355-1358.
Bundgaard (ed.), Design of Prodrugs, Elsevier (1985).
CLSI. 2008. Reference Method for Broth Dilution Antifungal Susceptibility Testing of Yeasts; Approved Standard—Third Edition. Clinical and Laboratory Standards Institute, CLSI document M27-A3.
Danby, et al., "Effect of pH on in vitro susceptibility of Candida glabrata and Candida albicans to 11 antifungal agents and implications for clinical use," Antimicrob Agents Chemother 56: 1403-1406 (2012).
DIFLUCAN® (Fluconazole Tablets) label, May 2011.
Foxman B, et al., Candida vaginitis: self-reported incidence and associated costs, Sex Transm Dis 2000, 27: 230-235 (2000).
Gennaro (ed.), Remington: The Science and Practice of Pharmacy, 20th edition (2000).
Guidance for Industry, Vulvovaginal Candidiasis—Developing Antimicrobial Drugs for Treatment, Draft Guidance, U.S. Department of Health and Human Services, Food and Drug Administration, Center for Drug Evaluation and Research (CDER), Jul. 1998, Clin-Anti.
Helou et al., "A multicentre, randomized, evaluator-blinded, active-controlled study to evaluate the safety and efficacy of oral SCY-078 in subjects with moderate to severe vulvovaginal candidiasis," abstract from 27th ECCMID, Vienna, Austria, Apr. 22-25, 2017, XP-002786003.
Larkin et al., "The effect of pH on the in vitro antifungal activity of SCY-078," Abstract, American Journal of Obstetrics & Gynecology, Dec. 2017.
Larkin et al., "The Effect of PH on the In Vitro Antifungal Activity of SCY-078," Poster, IDSOG, Aug. 2017.
Marr et al., The trailing end point phenotype in antifungal susceptibility testing is PH dependent, Antimicrob. Agents Chemother., 43: 1383-1386 (1999).
Onishi et al., "Discovery of Novel Antifungal (1,3)-β-D-Glucan Synthase Inhibitors," 44(2) Antimicrob. Agents Chemother. 368-377 (2000).
Pelaez et al., "The Discovery of Enfumafungin, a Novel Antifungal Compound Produced by an Endophytic Hormonema Species: Biological Activity and Taxonomy of the Producing Organisms," 23(3) Syst. Appl. Microbiol. 333-343 (2000).
Press release, "SCYNEXIS Announces Complete Results from Two Phase 2 Studies of Oral SCY-078 in Patients with *Candida* spp. Infections and Closing of a $15 Million Term Loan," Oct. 5, 2016.
Press release, "SCYNEXIS, Inc. Announces Positive Results in its Proof-of-Concept Phase 2 Study of SCY-078, the First Member of a Novel Class of Glucan Synthase Inhibitors," Jun. 8, 2016.

(Continued)

*Primary Examiner* — Alicia L Otton
(74) *Attorney, Agent, or Firm* — Covington & Burling LLP; Melody Wu; Jennifer L. Robbins

(57) ABSTRACT

Enfumafungin derivative triterpenoid antifungal compounds are used to treat or prevent fungal infections occurring in or under acidic conditions where the pH is lower than about 7, due to their unexpected, enhanced efficacy under such conditions. The enfumafungin derivative triterpenoids (or pharmaceutically acceptable salts or hydrates thereof) are inhibitors of (1,3)-β-D-glucan synthesis and are useful in the treatment or prevention of yeast or mold infections that occur in anatomic areas having a low pH, such as the vaginal cavity, or under acidic local environment conditions such of those seen in fungal abscesses, empyema, or upper gastrointestinal tract infections.

15 Claims, 1 Drawing Sheet

(56) References Cited

OTHER PUBLICATIONS

Press release, "SCYNEXIS Reports Positive Results from Phase 2b Dose-Finding Study of Oral SCY-078 in Vulvovaginal Candidiasis," Jul. 10, 2018.

Roman et al., "SCY-078 Phase 2 Study in Moderate and Severe Vulvovaginal Candidiasis (VVC)," poster from 27th ECCMID, Vienna, Austria, Apr. 22-25, 2017, XP-002786002.

Schwartz et al., "Isolation and Structural Determination of Enfumafungin, a Triterpene Glycoside Antifungal Agent That is a Specific Inhibitor of Glucan Synthesis," 122(16-20) J. Am. Chem. Soc. 4882-4886 (2000).

Schwartz, "Cell wall active antifungal agents," 11(11) Exp. Opin. Ther. Patents 1761-1772 (2001).

Sobel J., Vulvovaginal candidiasis, Lancet 369:1961-1971 (2007).

Wring et al., "Preclinical Pharmacokinetics and Pharmacodynamic Target of SCY-078, a First-in-Class Orally Active Antifungal Glucan Synthesis Inhibitor, in Murine Models of Disseminated Candidiasis," Antimicrobial Agents and Chemotherapy, vol. 61, No. 4, Jan. 30, 2017.

International Search Report and Written Opinion for PCT/US2018/044619 dated Nov. 6, 2018.

Helou S., Angulo D. "A multicenter, randomized, evaluator blinded, active-controlled study to evaluate the safety and efficacy of oral SCY-078 vs. oral fluconazole in 96 subjects with moderate to severe vulvovaginal candidiasis." American Journal of Obstetrics & Gynecology Dec. 2017, IDSOG Abstracts, Item 19 [P720-721].

Antifungal Susceptibility at Different pH Conditions for Vaginal *Candida* spp. Isolates
(adapted from Danby et al. (2012))

| Type (# of isolates tested) | pH | Value (µg/ml) | | | |
|---|---|---|---|---|---|
| | | Fluconazole $MIC_{50}$ | Itraconazole $MIC_{50}$ | Voriconazole $MIC_{50}$ | Posaconazole $MIC_{50}$ |
| Fluconazole - resistant *C. glabrata* (40) | 7 | 8 | 0.125 | 0.125 | 0.125 |
| | 4 | >64 | 1 | 8 | 4 |
| Fluconazole - resistant *C. albicans* (10) | 7 | 2 | 0.03 | 0.03 | 0.03 |
| | 4 | 32 | 0.03 | 2 | 0.03 |
| Fluconazole - sensitive *C. albicans* (15) | 7 | 0.125 | - | 0.03 | 0.03 |
| | 4 | 1 | - | 0.03 | 0.03 |

| Type (# of isolates tested) | pH | Value (µg/ml) | | | |
|---|---|---|---|---|---|
| | | Ketoconazole $MIC_{50}$ | Amphotericin B $MIC_{50}$ | Flucytosine $MIC_{50}$ | Caspofungin $MIC_{50}$ |
| Fluconazole - resistant *C. glabrata* (40) | 7 | 0.06 | 0.125 | 0.125 | 0.5 |
| | 4 | >16 | 4 | 0.125 | 0.5 |
| Fluconazole - resistant *C. albicans* (10) | 7 | 0.03 | 0.5 | 1 | 0.06 |
| | 4 | 0.5 | 16 | 0.5 | 0.06 |
| Fluconazole - sensitive *C. albicans* (15) | 7 | - | 0.25 | 0.125 | 0.06 |
| | 4 | - | 8 | 0.125 | 0.06 |

ANTIFUNGAL AGENTS WITH ENHANCED ACTIVITY IN ACIDIC PH

FIELD OF THE INVENTION

The present invention relates to the use of enfumafungin derivative triterpenoid antifungal compounds to treat or prevent fungal infections that occur in or under acidic conditions where the pH is lower than about 7. More particularly, the invention relates to the use of enfumafungin derivative triterpenoids (or pharmaceutically acceptable salts or hydrates thereof) that are inhibitors of (1,3)-β-D-glucan synthesis, in the treatment or prevention of yeast or mold infections that occur in conditions or anatomic areas that have acidic pH; such infections include vaginal yeast infections in which the pH is typically from about 4 to about 4.5, abscesses in which the pH is typically from about 5.5 to about 6.8, and infections of the upper gastrointestinal tract. An antifungal agent that shows enhanced antifungal potency in acidic pH is expected to provide an advantage in the treatment of fungal infections occurring under low pH conditions, such as vulvovaginal candidiasis (VVC), abscesses, and infections of the upper gastrointestinal tract.

BACKGROUND OF THE INVENTION

Fungal infections are a major healthcare problem and are most commonly manifested as invasive or systemic fungal disease (e.g., candidemia, invasive aspergillosis), localized fungal infections (e.g., pleural empyema and abscess localized in abdomen, brain, lung, etc.) and mucocutaneous infections (e.g., oral, esophageal and vulvovaginal candidiasis). The type and scope of the infection depends on the virulence factors of the fungal pathogen, the host's defenses, and the anatomic areas involved.

Severe systemic or invasive fungal infections are more common in immune-compromised patients such as patients receiving chemotherapy to treat malignancies, or receiving immunomodulatory agents to treat chronic inflammatory conditions, or suffering from immune deficiencies, either acquired or due to genetic disorders. Despite currently available antifungal therapies, systemic fungal infections are associated with a mortality rate of up to 50%, depending on the pathogen and the underlying condition of the patient.

Localized fungal infections typically originate via dissemination of yeast from a local area where they normally colonize to an area that is normally sterile (e.g., abscess in abdominal cavity after gut perforation or surgery) or from fungi entering the blood or lymphatic system that reaches a particular organ (e.g., lung, liver, spleen) and develops a deep seated infection. Abscesses secondary to gastrointestinal leakage after trauma or surgery are often mixed infections with involvement of *Candida* spp. and bacteria and commonly have a low pH within the abscess (e.g., a pH that is between about 5.5 to about 6.8 within the abscess).

Mucocutaneous fungal infections can occur in immuno-compromised as well as in non-compromised individuals. The most common mucocutaneous fungal infections are vulvovaginal yeast infections, which are predominantly caused by species of *Candida* and are commonly referred to as vulvovaginal candidiasis (VVC). VVC is estimated to affect 70% to 75% of women at least once during their lifetimes (Sobel J., *Vulvovaginal candidiasis*, Lancet 369: 1961-71 (2007)), and although not life-threatening, it can have a substantial impact on the quality of life in the affected individuals, particularly in those suffering recurrent episodes. The diagnosis and treatment of VVC, along with loss of productivity due to the condition, are estimated to cost ~$1 billion in the USA (Foxman B, et al., *Candida vaginitis: self-reported incidence and associated costs*, Sex Transm Dis 2000, 27: 230-35 (2000)). While most women present only sporadic episodes of VVC, some women have more chronic manifestations and/or recurrent episodes commonly referred to as recurrent VVC (rVVC). Several topical and two oral antifungal agents (fluconazole and itraconazole) are approved for the treatment of VVC globally, although there is no approved therapy for rVVC. In the USA, fluconazole is the only oral treatment approved for VVC, and globally, it is the most commonly used oral antifungal agent used to treat this condition. However, in a study of oral fluconazole reported in Diflucan®'s label, therapeutic cure, defined in the study as complete resolution of signs and symptoms, and negative potassium hydroxide examination and negative culture, was only achieved in approximately half of VVC cases. See Diflucan® (fluconazole) label (May 2011). The pH of the vaginal milieu is acidic (pH from about 4 to about 4.5) and remains unchanged during *Candida* spp. infections; this low pH environment is considered to be at least in part responsible for the suboptimal therapeutic outcomes with current antifungal therapies for VVC (Danby C S, et al., *Effect of pH on in vitro susceptibility of Candida glabrata and Candida albicans to 11 antifungal agents and implications for clinical use*, Antimicrob Agents Chemother 56: 1403-6 (2012)).

The potency of an antifungal agent, expressed as the minimum inhibitory concentration (MIC) shown to inhibit the growth of an organism in 50% ($MIC_{50}$) or 90% ($MIC_{90}$) of the isolates tested, is frequently affected by pH. Considering the variability due to the methods used to determine MICs, the clinical relevance of differences in MICs in either direction that are 4-fold or smaller may be difficult to establish, such that a 4-fold difference, for example, may not be clinically significant. On the other hand, changes greater than 4-fold are generally considered to be clinically meaningful and are likely significant. Given that the pH of the environments where infections occur can vary and may have an effect on the clinical efficacy of antifungal agents intended to treat the infections, the impact of pH on antifungal potency has been studied and reported. Although most of the investigations regarding antifungal activity at low pH have focused on isolates causing VVC, the same *Candida* species cause other infections in which the pH is expected to be acidic (e.g., abdominal abscesses, esophageal candidiasis with reflux, pleural empyema, etc.); accordingly, the findings from these reports demonstrating the decreased potency of antifungals at low pH are expected to be applicable to a broader array of clinical conditions where low pH is a common factor.

Danby et al. (2012) conducted a very comprehensive study evaluating the effect of pH on the antifungal potency of 11 antifungal agents against the most common *Candida* species causing VVC. Results from that study indicated that for most of the antifungal agents, there was an increase in MICs (e.g., greater than 4-fold) indicative of a decrease in antifungal potency under acidic conditions (e.g., pH of 4) when compared to neutral pH conditions (e.g., pH of 7). Generally, all of the antifungals belonging to the azole chemical class, and particularly fluconazole (the only available oral azole agent for VVC in most of the world), were significantly affected by this phenomenon, indicating that many *Candida* strains that would be considered susceptible when the infection occurs in neutral pH conditions (e.g., pH of about 7) are resistant when the pH environment is acidic (e.g., pH of about 4-4.5), such as in VVC. (See FIG. 1, adapted from Danby et al. (2012), regarding antifungal susceptibility at different pH conditions for vaginal Candida spp. isolates.) Danby C, et al. (2012) concluded that the decrease in antifungal potency at acidic pH is an important factor to explain the lack of efficacy of some antifungal agents in VVC, where the pH is typically from about 4 to 4.5. Although some of the antifungal agents tested in this experiment by Danby et al. (2012) appeared to be less affected by the lowering of the pH, none showed a significant increase in antifungal potency (e.g., >4-fold decrease in MIC) under acidic conditions.

The impact of pH on antifungal potency and its potential implications for treatment of VVC has also been reported by Boikov, et al., In vitro activity of the novel echinocandin CD101 at pH 7 and 4 against Candida spp. isolates from patients with vulvovaginal candidiasis, J Antimicrob Chemother 72: 1355-1358 (2017). In the Boikov et al. study, the anti-fungal activity of azoles approved for VVC (fluconazole and itraconazole), as well as three approved echinocandins (caspofungin, micafungin, and anidulafungin) and one echinocandin in development (CD101) were evaluated at pH 7 and pH 4 against Candida species commonly associated with VVC. Performance of both azoles and echinocandins (the only glucan synthesis inhibitors available) was negatively affected by low pH, confirming the results from earlier studies that this phenomenon is not unique to one antifungal class (azoles), although some drug classes seem more affected than others. In addition, consistent with results reported previously, there was no instance of significant increase in antifungal potency (e.g., >4-fold decrease in MIC) under acidic conditions. Thus, the general expectation from the art is that the potency of antifungals is negatively affected at least to some degree by low pH conditions.

Enfumafungin is a hemiacetal triterpene glycoside that is produced in fermentations of a Hormonema spp. associated with living leaves of Juniperus communis (U.S. Pat. No. 5,756,472; Pelaez et al., Systematic and Applied Microbiology, 23:333-343 (2000); Schwartz et al., JACS, 122: 4882-4886 (2000); Schwartz, R. E., Expert Opinion on Therapeutic Patents, 11(11): 1761-1772 (2001)). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase (Onishi et al., Antimicrobial Agents and Chemotherapy, 44: 368-377 (2000); Pelaez et al., (2000)). 1,3-β-D-glucan synthase remains an attractive target for antifungal drug action because it is present in many pathogenic fungi and therefore affords a broad antifungal spectrum. In addition, because there is no mammalian counterpart to (1,3)-β-D-glucan synthase, the enfumafungin derivatives described herein have little or no mechanism-based toxicity. The triterpenoid compound derivatives of enfumafungin used according to this invention have demonstrated activity against fungal isolates of Candida spp., including those isolates that are resistant to azoles or other glucan synthase inhibitors (e.g., lipopeptides agents such echinocandins), indicating that the biological and molecular target of the enfumafungin derivatives is different from that of other glucan synthase inhibitors.

Various enfumafungin derivatives have been disclosed, e.g., in International Patent Publication Nos. WO 2007/126900 and WO 2007/127012.

Certain representatives of these enfumafungin derivatives can be administered orally, have shown antifungal activity against Candida species, and have shown adequate distribution into tissues, including vaginal tissues. At the same time, however, previous studies show a general decrease in anti-fungal potency of various agents against Candida spp. in acidic pH environments, and more specifically in pH environments similar to the vaginal milieu (which has a pH of about 4-4.5). See Danby et al. (2012) and Boikov et al. (2017).

The anti-fungal activity of SCY-078, a representative compound of enfumafungin derivatives described herein, was evaluated in a feasibility study regarding the treatment of VVC.

As a first step of the feasibility evaluation, a proof-of-concept exploratory trial in 96 patients with moderate to severe acute VVC was conducted. Subjects received SCY-078 tablets orally, administered at a dose of 1250 mg on day 1, followed by 750 mg once a day for 2 or 4 days. A comparator group of patients receiving oral fluconazole at the approved dose (150 mg, single dose) was also included. Both dose regimens of SCY-078 showed similar activity. The efficacy results are summarized in the table below:

TABLE A

| Intent-to-Treat (ITT) Population | | |
|---|---|---|
|  | Combined SCY-078 (n = 64) | Fluconazole (n = 32) |
| Clinical cure* | 78.1% | 65.6% |
| Mycological eradication* | 70.3% | 68.8% |
| Therapeutic cure* | 56.3% | 56.3% |

*In this study, clinical cure was defined as resolution of signs and symptoms of infection without further antifungal treatment (signs and symptoms that had a score of 2 or 1 at baseline should be 0, and signs and symptoms with a score of 3 at baseline should be 0 or 1, at the Test-of-Cure visit); mycological eradication was defined as a negative culture for the baseline yeast pathogen; and therapeutic cure was defined as both clinical cure and mycological eradication.

Given that various compounds, including all clinically relevant classes of antifungals available for use to date such as azoles, polyenes, and echinocandins, have shown reduced potency in acidic pH environments (Danby et al. (2012) and Boikov et al. (2017)), and more specifically in pH environments similar to the vaginal milieu (which has a pH of about 4-4.5), the anti-fungal activity of SCY-078 was evaluated in different pH conditions as a next step in the feasibility assessment for developing the enfumafungin derivative class of antifungals for fungal infections where low pH is expected.

There is a need in the art for antifungal therapy for humans, particularly in the treatment of fungal infections occurring under low pH conditions such as vulvovaginal candidiasis and infections of the gastrointestinal tract, in which the antifungal maintains potency in low pH conditions.

SUMMARY OF THE INVENTION

It was surprisingly found that the enfumafungin derived triterpenoid compound SCY-078—a representative compound of enfumafungin derivatives described herein—did not show decreased potency under low pH conditions. Moreover, the compound unexpectedly demonstrated increased activity under such conditions. The enfumafungin derived triterpenoid compound surprisingly exhibited significantly enhanced anti-fungal activity at a low pH representative of the vaginal environment (pH 4.5). In addition, SCY-078 showed good bioavailability and extensive tissue distribution following oral administration in mice. Such features are important for the treatment and prevention of fungal infections, including VVC, when such treatment or prevention involves oral administration.

The present invention relates to using enfumafungin derivatives for the treatment or prevention of fungal infections that occur in or under acidic conditions (e.g., pH lower than about 5). Enfumafungin derivatives, and pharmaceutically acceptable salts or hydrates thereof, are useful in the inhibition of (1,3)-β-D-glucan synthase, and are particularly useful in the prevention or treatment of fungal infections that occur under acidic local conditions, for example where the pH is about 5 or lower, which are infection situations where potent antifungal activity is needed in the art.

The present invention addresses needs in the art such as those described above because the enfumafungin derivatives described herein (a) not only unexpectedly retain activity in acidic pH, but (b) even more surprisingly, demonstrate significantly enhanced antifungal potency under low pH conditions. These properties are particularly useful and relevant in the treatment of fungal infections in areas where acidic pH is expected, and where other antifungals would be expected to have decreased potency due to the low pH local environment. Some examples of fungal infections where a low-pH environment is expected include, but are not limited to, vulvovaginal candidiasis (VVC), abdominal abscess, pleural empyema, lung abscess, liver abscess, and oropharyngeal or esophageal abscess.

Applications of this invention include but are not limited to the ability to more easily achieve, at the infection site, concentrations (of the enfumafungin derivatives) that are effective to treat or prevent a fungal infection under acidic conditions (e.g., to more easily achieve concentrations above the MICs needed to treat or prevent a fungal infection under acidic conditions) because the anti-fungal activity of these compounds surprisingly is enhanced under acidic conditions. Because anti-fungal activity is enhanced under acidic conditions, MICs of the present enfumafungin derivatives required to treat or prevent an infection under low pH conditions are lower than the MICs of the enfumafungin derivatives required to treat or prevent an infection at pH conditions of about 7. The present invention also makes it possible, in treating or preventing a fungal infection that occurs under acidic pH conditions (for example, at a pH of about 5 or lower), to administer doses of the enfumafungin derivative that are lower than the doses required to treat a fungal infection under pH conditions of about 7.

The present invention provides the use of a compound of Formula (I), or a pharmaceutically acceptable salt or hydrate thereof:

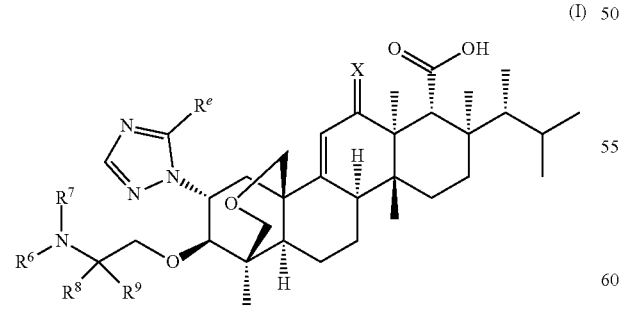

(I)

wherein:

X is O or H, H;

$R^e$ is C(O)NR$^f$R$^g$ or a 6-membered ring heteroaryl group containing 1 or 2 nitrogen atoms wherein the heteroaryl group is optionally mono-substituted on a ring carbon with fluoro or chloro or on a ring nitrogen with oxygen;

$R^f$, $R^g$, $R^6$ and $R^7$ are each independently hydrogen or $C_1$-$C_3$ alkyl;

$R^8$ is $C_1$-$C_4$ alkyl, $C_3$-$C_4$ cycloalkyl or $C_4$-$C_5$ cycloalkylalkyl;

$R^9$ is methyl or ethyl; and $R^8$ and $R^9$ are optionally taken together to form a 6-membered saturated ring containing 1 oxygen atom, in a subject for the treatment or prevention of a fungal infection that occurs under acidic pH conditions. The fungal infection may be a yeast or mold infection that occurs in conditions or anatomic areas that have a pH lower than about 7, including, for example, a pH of about 5, about 4.5, or about 4. Such infections include but are not limited to vaginal yeast infections, fungal abscess or empyema in any location, and infections in the upper gastrointestinal tract.

The invention also provides methods of treating or preventing a fungal infection that occurs under acidic pH conditions in a subject by administering the compound of Formula (I) or a pharmaceutically acceptable salt or hydrate thereof. Further, the invention provides the use of a compound of Formula (I) or a pharmaceutically acceptable salt or hydrate thereof in the preparation of a medicament for treating a fungal infection that occurs under acidic pH conditions in a subject.

BRIEF DESCRIPTION OF THE DRAWINGS

FIG. 1 is a table showing antifungal susceptibility at different pH conditions for vaginal *Candida* spp. isolates, adapted from Danby et al. (2012).

DETAILED DESCRIPTION OF THE INVENTION

Previous reports have shown that the potency of most antifungal agents decreases at low pH. No antifungal to date has shown a significant increase in potency (for example, as shown by a >4-fold reduction in MIC) when tested against *Candida glabrata* and *Candida albicans* (the most common *Candida* species causing infections in humans) in acidic conditions. Unexpectedly, enfumafungin derivatives described herein show a significant enhancement in their antifungal potency when tested at low pH, providing the basis for an unexpected clinical benefit when using the compounds in the treatment or prevention of fungal infections under low pH conditions. Examples of a potential clinical benefit of the enhanced activity of enfumafungin derivatives under acidic conditions include but are not limited to: improved efficacy in treating or preventing fungal infections occurring under acidic conditions, enhanced likelihood to achieve tissue concentrations that are above the MIC of the causative fungal pathogen (providing a greater opportunity to kill or prevent the growth of the pathogen), and the opportunity to achieve successful outcomes while administering doses of the enfumafungin derivatives that are lower than the doses that would be required to treat or prevent an infection under neutral pH conditions.

The present invention provides the use of a compound of Formula (I), or a pharmaceutically acceptable salt or hydrate thereof:

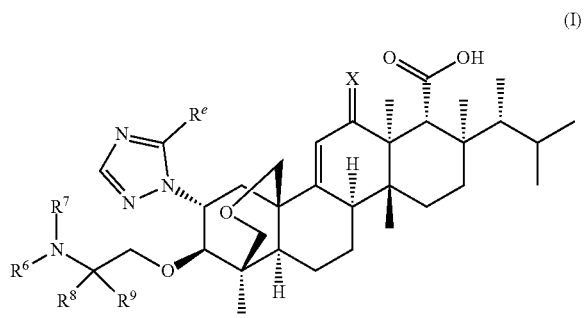

wherein:

X is O or H, H;

$R^e$ is $C(O)NR^fR^g$ or a 6-membered ring heteroaryl group containing 1 or 2 nitrogen atoms wherein the heteroaryl group is optionally mono-substituted on a ring carbon with fluoro or chloro or on a ring nitrogen with oxygen;

$R^f$, $R^g$, $R^6$ and $R^7$ are each independently hydrogen or $C_1$-$C_3$ alkyl;

$R^8$ is $C_1$-$C_4$ alkyl, $C_3$-$C_4$ cycloalkyl or $C_4$-$C_5$ cycloalkylalkyl;

$R^9$ is methyl or ethyl; and $R^8$ and $R^9$ are optionally taken together to form a 6-membered saturated ring containing 1 oxygen atom, in a subject for the treatment or prevention of a fungal infection that occurs under acidic pH conditions. The fungal infection may be a yeast or mold infection that occurs in conditions or anatomic areas that have a pH lower than about 7, such as, for example, a pH between about 4 to about 6.8. In some embodiments, the pH ranges from about 4 to about 6; and in certain embodiments, such as vaginal yeast infections, the pH is lower than about 5, and more specifically may be between about 4 to about 4.5. Infections treatable and/or preventable by the methods of the present invention include but are not limited to vaginal yeast infections, fungal abscess or empyema in any location, and infections in the upper gastrointestinal tract.

The invention also provides methods of treating or preventing a fungal infection that occurs under acidic pH conditions in a subject by administering the compound of Formula (I) or a pharmaceutically acceptable salt or hydrate thereof. Further, the invention provides the use of a compound of Formula (I) or a pharmaceutically acceptable salt or hydrate thereof in the preparation of a medicament for treating a fungal infection that occurs under acidic pH conditions in a subject.

The present invention also provides the use of a compound of Formula (Ia), or a pharmaceutically acceptable salt or hydrate thereof:

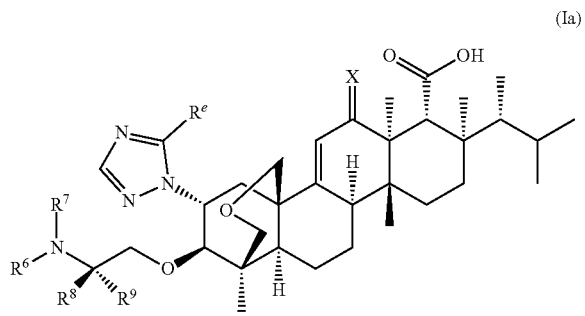

wherein the substituents are as provided for in Formula (I), in a subject for the treatment or prevention of a fungal infection that occurs under acidic pH conditions. The fungal infection may be a yeast or mold infection that occurs in conditions or anatomic areas that have a pH lower than about 7, such as, for example, a pH between about 4 to about 6.8. In some embodiments, the pH ranges from about 4 to about 6; and in certain embodiments, such as vaginal yeast infections, the pH is lower than about 5, and more specifically may be between about 4 to about 4.5. Infections treatable and/or preventable by the methods of the present invention include but are not limited to vaginal yeast infections, fungal abscess or empyema in any location, and infections in the upper gastrointestinal tract.

The invention also provides methods of treating or preventing a fungal infection that occurs under acidic pH conditions in a subject by administering the compound of Formula (Ia) or a pharmaceutically acceptable salt or hydrate thereof. Further, the invention provides the use of a compound of Formula (Ia) or a pharmaceutically acceptable salt or hydrate thereof in the preparation of a medicament for treating a fungal infection that occurs under acidic pH conditions in a subject.

In embodiment 1: X is H, H, and the other substituents are as provided in Formula (I).

In embodiment 2: $R^e$ is either pyridyl or pyrimidinyl optionally mono-substituted on a ring carbon with fluoro or chloro or on a ring nitrogen with oxygen, and the other substituents are as provided in embodiment 1 or in Formula (I).

In embodiment 3: $R^e$ is 4-pyridyl and the other substituents are as provided in embodiment 1 or in Formula (I).

In embodiment 4: $R^e$ is $C(O)NH_2$ or $C(O)NH(C_1$-$C_3$ alkyl) and the other substituents are as provided in embodiment 1 or in Formula (I).

In embodiment 5: $R^8$ is $C_1$-$C_4$ alkyl and $R^9$ is methyl; and the other substituents are as provided in embodiment 1, 2, 3, or 4, or in Formula (I).

In embodiment 6: $R^8$ is t-butyl, $R^9$ is methyl; and the other substituents are as provided in embodiment 1, 2, 3, or 4, or in Formula (I).

In embodiment 7: $R^6$ and $R^7$ are each independently hydrogen or methyl and the other substituents are as provided in embodiment 1, 2, 3, 4, 5, or 6, or in Formula (I).

In embodiment 1': X is H, H, and the other substituents are as provided for in Formula (Ia).

In embodiment 2': $R^e$ is either pyridyl or pyrimidinyl optionally mono-substituted on a ring carbon with fluoro or chloro or on a ring nitrogen with oxygen, and the other substituents are as provided in embodiment 1' or in Formula (Ia).

In embodiment 3': $R^e$ is 4-pyridyl and the other substituents are as provided in embodiment 1' or in Formula (Ia).

In embodiment 4': $R^e$ 's $C(O)NH_2$ or $C(O)NH(C_1$-$C_3$ alkyl) and the other substituents are as provided in embodiment 1' or in Formula (Ia).

In embodiment 5': $R^8$ is $C_1$-$C_4$ alkyl and $R^9$ is methyl; and the other substituents are as provided in embodiment 1', 2', 3', or 4', or in Formula (Ia).

In embodiment 6': $R^8$ is t-butyl, $R^9$ is methyl; and the other substituents are as provided in embodiment 1', 2', 3', or 4', or in Formula (Ia).

In embodiment 7': $R^6$ and $R^7$ are each independently hydrogen or methyl and the other substituents are as provided in embodiment 1', 2', 3', 4', 5', or 6', or in Formula (Ia).

In preferred embodiments, the present invention provides the use of a compound of Formula (II):

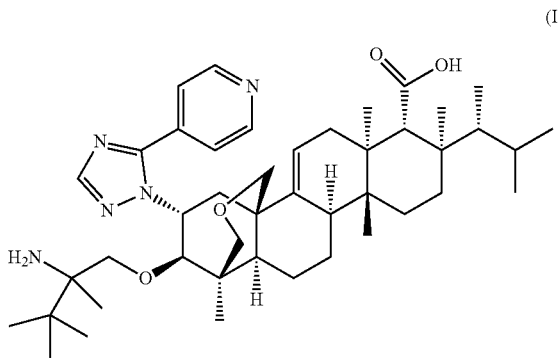

(II)

which is (1S,4aR,6aS,7R,8R,10aR,10bR,12aR,14R,15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, or a pharmaceutically acceptable salt or hydrate thereof, in a subject for the treatment or prevention of a fungal infection that occurs under acidic pH conditions. The fungal infection may be a yeast or mold infection that occurs in conditions or anatomic areas that have a pH lower than about 7, such as, for example, a pH between about 4 to about 6.8. In some embodiments, the pH ranges from about 4 to about 6; and in certain embodiments, such as vaginal yeast infections, the pH is lower than about 5, and more specifically may be between about 4 to about 4.5. Infections treatable and/or preventable by the methods of the present invention include but are not limited to vaginal yeast infections, fungal abscess or empyema in any location, and infections in the upper gastrointestinal tract.

The invention also provides methods of treating or preventing a fungal infection that occurs under acidic pH conditions in a subject by administering the compound of Formula (II) or a pharmaceutically acceptable salt or hydrate thereof. Further, the invention provides the use of a compound of Formula (II) or a pharmaceutically acceptable salt or hydrate thereof in the preparation of a medicament for treating a fungal infection that occurs under acidic pH conditions in a subject.

In other preferred embodiments, the present invention provides the use of a compound of Formula (IIa) (herein referred to as SCY-078):

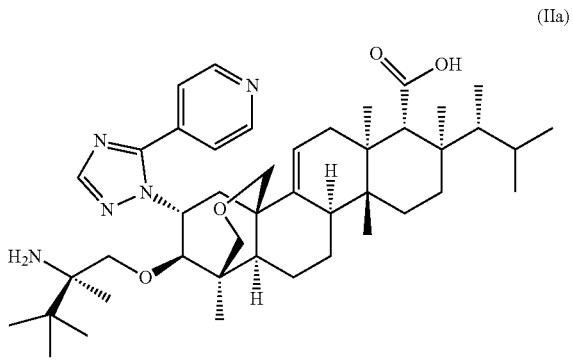

(IIa)

which is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, or a pharmaceutically acceptable salt or hydrate thereof, in a subject for the treatment or prevention of a fungal infection that occurs under acidic pH conditions. The fungal infection may be a yeast or mold infection that occurs in conditions or anatomic areas that have a pH lower than about 7, such as, for example, a pH between about 4 to about 6.8. In some embodiments, the pH ranges from about 4 to about 6; and in certain embodiments, such as vaginal yeast infections, the pH is lower than about 5, and more specifically may be between about 4 to about 4.5. Infections treatable and/or preventable by the methods of the present invention include but are not limited to vaginal yeast infections, fungal abscess or empyema in any location, and infections in the upper gastrointestinal tract.

The invention also provides methods of treating or preventing a fungal infection that occurs under acidic pH conditions in a subject by administering the compound of Formula (IIa) or a pharmaceutically acceptable salt or hydrate thereof. Further, the invention provides the use of a compound of Formula (IIa) or a pharmaceutically acceptable salt or hydrate thereof in the preparation of a medicament for treating a fungal infection that occurs under acidic pH conditions in a subject.

In preferred embodiments, the phosphate salt of a compound of Formula (I), (Ia), (II), or (IIa) is used or administered as described herein.

In preferred embodiments, the citrate salt of a compound of Formula (I), (Ia), (II), or (IIa) is used or administered as described herein.

The present invention also provides the use of a pharmaceutical composition comprising a compound of Formula (I), (Ia), (II), or (IIa), or a pharmaceutically acceptable salt or hydrate thereof, and a pharmaceutically acceptable carrier, adjuvant, or vehicle, in a subject for the treatment or prevention of a fungal infection that occurs under acidic pH conditions. The fungal infection may be a yeast or mold infection that occurs in conditions or anatomic areas that have a pH lower than about 7, such as, for example, a pH ranging from about 4 to about 6, or more specifically a pH of about 5, about 4.5, or about 4. Such infections include but are not limited to vaginal yeast infections, fungal abscess or empyema in any location, and infections in the upper gastrointestinal tract. For example, the pH in the vaginal milieu is about 4-4.5, and the pH of abscesses can range from about 5.5 to about 6.8.

The invention also provides methods of treating or preventing a fungal infection that occurs under acidic pH conditions in a subject by administering a pharmaceutical composition comprising the compound of Formula (I), (Ia), (II), or (IIa), or a pharmaceutically acceptable salt or hydrate thereof.

In the description of compounds in the embodiments set forth above, indicated substitutions are included only to the extent that the substituents provide stable compounds consistent with the definition.

The compounds of Formula (I), (Ia), (II), and (IIa), and pharmaceutically acceptable salts and/or hydrate forms thereof, have antimicrobial (e.g., antifungal) activities against yeasts and other fungi, including one or more of *Acremonium*, *Absidia* (e.g., *Absidia corymbifera*), *Alternaria*, *Aspergillus* (e.g., *Aspergillus clavatus*, *Aspergillus flavus*, *Aspergillus fumigatus*, *Aspergillus nidulans*, *Aspergillus niger*, *Aspergillus terreus*, and *Aspergillus versicolor*),

*Bipolaris, Blastomyces* (e.g., *Blastomyces dermatitidis*), *Blastoschizomyces* (e.g., *Blastoschizomyces capitatus*), *Candida* (e.g., *Candida albicans, Candida glabrata, Candida guilliermondii, Candida kefyr, Candida krusei, Candida lusitaniae, Candida parapsilosis, Candida pseudotropicalis, Candida stellatoidea, Candida tropicalis, Candida utilis, Candida lipolytica, Candida famata* and *Candida rugosa*), *Cladosporium* (e.g., *Cladosporium carrionii* and *Cladosporium trichloides*), *Coccidioides* (e.g., *Coccidioides immitis*), *Cryptococcus* (e.g., *Cryptococcus neoformans*), *Curvularia, Cunninghamella* (e.g., *Cunninghamella elegans*), *Dermatophyte, Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candiddum* and *Geotrichum clavatum*), *Histoplasma* (e.g., *Histoplasma capsulatum* var. *capsulatum*), *Malassezia* (e.g., *Malassezia furfur*), *Microsporum* (e.g., *Microsporum canis* and *Microsporum gypseum*), *Mucor, Paracoccidioides* (e.g., *Paracoccidioides brasiliensis*), *Penicillium* (e.g., *Penicillium marneffei*), *Phialophora, Pityrosporum ovale, Pneumocystis* (e.g., *Pneumocystis carinii*), *Pseudallescheria* (e.g., *Pseudallescheria boydii*), *Rhizopus* (e.g., *Rhizopus microsporus* var. *rhizopodiformis* and *Rhizopus oryzae*), *Saccharomyces* (e.g., *Saccharomyces cerevisiae*), *Scedosporium* (e.g., *Scedosporium apiosperum*), *Scopulariopsis, Sporothrix* (e.g., *Sporothrix schenckii*), *Trichoderma, Trichophyton* (e.g., *Trichophyton mentagrophytes* and *Trichophyton rubrum*), and *Trichosporon* (e.g., *Trichosporon asahii, Trichosporon beigelii* and *Trichosporon cutaneum*). The compounds are not only useful against organisms causing systemic human pathogenic fungal infections, but also are useful against organisms causing superficial fungal infections such as Trichoderma spp. and other *Candida* spp. The compounds are particularly effective against *Candida* species and *Aspergillus* species.

In view of their antifungal activity, compounds of Formula (I), (Ia), (II), and (IIa), and pharmaceutically acceptable salts and/or hydrate forms thereof, are useful for the treatment and/or prevention of one or more of a variety of superficial, cutaneous, mucocutaneous, subcutaneous and systemic fungal infections in vulva, vagina, skin, eye, hair, nail, oral mucosa, gastrointestinal tract, bronchus, lung, pleura, peritoneum, endocardium, brain, meninges, urinary organ, vaginal portion, oral cavity, systemic, kidney, bronchus, heart, external auditory canal, bone, nasal cavity, paranasal cavity, spleen, liver, hypodermal tissue, lymph duct, gastrointestinal, articulation, muscle, tendon, interstitial plasma cell in lung, blood, and so on.

The compounds of Formula (I), (Ia), (II), and (IIa), and pharmaceutically acceptable salts and/or hydrate forms thereof, are useful for preventing and treating one or more of various infectious diseases, such as vulvovaginal candidiasis (VVC), dermatophytosis (e.g., trichophytosis, ringworm or tinea infections), paronychia, pityriasis versicolor, erythrasma, intertrigo, fungal diaper rash, candida vulvitis, candida balanitis, otitis externa, candidiasis (cutaneous and mucocutaneous), chronic mucocandidiasis (e.g., thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, fungal keratitis, otomycosis, pneumocystosis, fungal abscess, fungal pleural empyema, and fungemia. The compounds of Formula (I), (Ia), (II), and (IIa), and pharmaceutically acceptable salts and/or hydrate forms thereof, may also be used as prophylactic agents to prevent systemic and topical fungal infections.

The compounds of Formula (I), (Ia), (II), and (IIa), and pharmaceutically acceptable salts and/or hydrate forms thereof, may be used to prevent recurrences of VVC in patients suffering from recurrent VVC. Use as prophylactic agents may, for example, be appropriate as part of a selective gut decontamination regimen in the prevention of infection in immuno-compromised patients (e.g., AIDS patients, patients receiving cancer therapy, or transplant patients). Prevention of fungal overgrowth during antibiotic treatment may also be desirable in some disease syndromes or iatrogenic states. Specifically, prevention of *Candida* spp. overgrowth in vagina in patients receiving antibiotic treatment or who have uncontrolled risk factors for *Candida* spp. overgrowth such as high glucose in blood, may be desirable.

The compounds of Formula (I), (Ia), (II), and (IIa), and pharmaceutically acceptable salts and/or hydrate forms thereof, can be made according to the synthesis methods disclosed in U.S. Pat. No. 8,188,085, the contents of which are hereby incorporated by reference in their entirety.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "cycloalkyl" refers to any cyclic ring of an alkane having a number of carbon atoms in the specified range. Thus, for example, "$C_{3-4}$ cycloalkyl" (or "$C_3$-$C_4$ cycloalkyl") refers to cyclopropyl and cyclobutyl.

The term "cycloalkyl-alkyl" (or equivalently "alkyl-cycloalkyl") as used herein refers to a system that includes an alkyl portion as described above and also includes a cycloalkyl portion as described above. Attachment to a "cycloalkyl-alkyl" (or "alkyl-cycloalkyl") may be through either the cycloalkyl or the alkyl portion. The specified number of carbon atoms in "cycloalkyl-alkyl" systems refers to the total number of carbon atoms in both the alkyl and the cycloalkyl parts. Examples of $C_4$-$C_5$ cycloalkyl-alkyl include but are not limited to methylcyclopropyl, dimethylcyclopropyl, methylcyclobutyl, ethylcyclopropyl, cyclopropylmethyl, cyclopropylethyl and cyclobutylmethyl.

The term "halogen" (or "halo") refers to fluorine, chlorine, bromine and iodine (alternatively referred to as fluoro, chloro, bromo, and iodo).

The term "or" as used herein denotes alternatives that may, where appropriate, be combined.

Unless expressly stated to the contrary, all ranges cited herein are inclusive. For example, a heterocyclic ring described as containing from "1 to 4 heteroatoms" means the ring can contain 1, 2, 3, or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

Any of the various cycloalkyl and heterocyclic/heteroaryl rings and ring systems defined herein may be attached to the rest of the compound at any ring atom (i.e., any carbon atom or any heteroatom) provided that a stable compound results.

Suitable 5- or 6-membered heteroaromatic rings include, but are not limited to, pyridyl, pyrazinyl, pyrimidinyl, pyridazinyl and triazolyl.

A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject). Reference to a compound also includes stable complexes of the compound such as a stable hydrate.

As a result of the selection of substituents and substituent patterns, certain of the compounds of Formula (I), (Ia), (II), and (IIa) can have asymmetric centers and can occur as mixtures of stereoisomers, or as individual diastereomers, or enantiomers. Unless otherwise indicated, all isomeric forms of these compounds (and pharmaceutically acceptable salts and/or hydrate forms thereof), whether isolated or in mixtures, are within the scope of the present invention. Also included within the scope of the present invention are tautomeric forms of the compounds as depicted (and pharmaceutically acceptable salts and/or hydrate forms thereof).

When any variable occurs more than one time in any constituent or in Formula (I), (Ia), (II), or (IIa), its definition on each occurrence is independent of its definition at every other occurrence. Also, combinations of substituents and/or variables are permissible only if such combinations result in stable compounds.

The term "substituted" includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., an aryl, a cycloalkyl, a heteroaryl, or a heterocyclyl) provided such ring substitution is chemically allowed and results in a stable compound.

A bond terminated by a wavy line is used herein to signify the point of attachment of a substituent group or partial structure. This usage is illustrated by the following example:

salts" or hydrates as appropriate. Other salts may, however, be useful in the preparation of the compounds or of their pharmaceutically acceptable salts. For example, when the compounds contain a basic amine group, they may be conveniently isolated as trifluoroacetic acid salts (e.g., following HPLC purification). Conversion of the trifluoroacetic acid salts to other salts, including pharmaceutically acceptable salts, may be accomplished by a number of standard methods known in the art. For example, an appropriate ion exchange resin may be employed to generate the desired salt. Alternatively, conversion of a trifluoroacetic acid salt to the parent free amine may be accomplished by standard methods known in the art (e.g., neutralization with an appropriate inorganic base such as $NaHCO_3$). Other desired amine salts may then be prepared in a conventional manner by reacting the free base with a suitable organic or inorganic acid. Representative pharmaceutically acceptable quaternary ammonium salts include the following: hydrochloride, sulfate, phosphate, carbonate, acetate, tartrate, citrate, malate, succinate, lactate, stearate, fumarate, hippurate, maleate, gluconate, ascorbate, adipate, gluceptate, glutamate, glucoronate, propionate, benzoate, mesylate, tosylate, oleate, lactobionate, laurylsulfate, besylate, caprylate, isetionate, gentisate, malonate, napsylate, edisylate, pamoate, xinafoate, napadisylate, hydrobromide, nitrate, oxalate, cinnamate, mandelate, undecylenate, and camsylate. Many of the compounds of Formula (I), (Ia), (II), and (IIa) carry an acidic carboxylic acid moiety, in which case suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The present invention includes within its scope the use of prodrugs of Formula (I), (Ia), (II), and (IIa). In general, such prodrugs will be functional derivatives of the compounds, which are readily convertible in vivo into the required compound. Thus, in the methods of treatment of the present

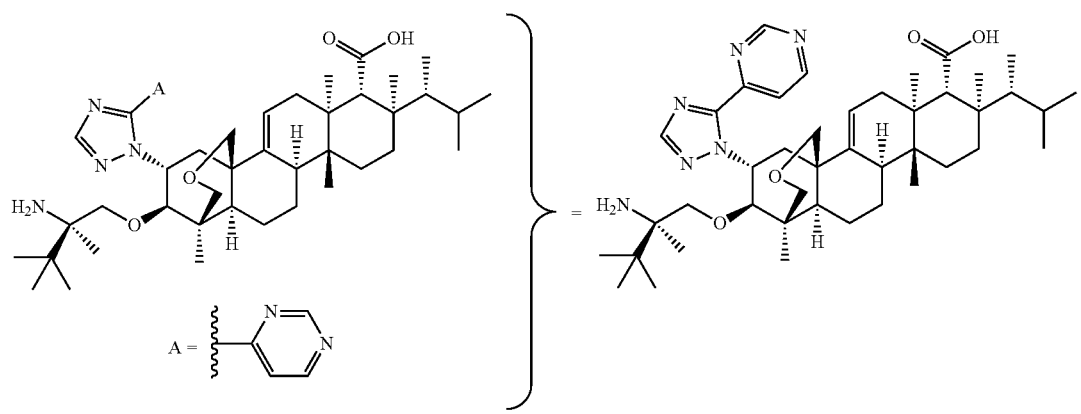

The compounds of Formula (I), (Ia), (II), and (IIa), and pharmaceutically acceptable salts and/or hydrate forms thereof, are also useful in the preparation and execution of screening assays for antifungal compounds. For example, the compounds are useful for isolating mutants, which are excellent screening tools for identifying further antifungal compounds.

The compounds of Formula (I), (Ia), (II), and (IIa) may be administered in the form of "pharmaceutically acceptable invention, the term "administering" shall encompass the treatment of the various conditions described with the compound specifically disclosed or with a compound that converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of the compounds of Formula (I), (Ia), (II), and (IIa) include active species produced upon introduction of the compounds into the biological milieu.

The term "administration" and variants thereof (e.g., "administering" a compound) mean providing a compound (optionally in the form of a salt or hydrate thereof) or a prodrug of the compound to the subject in need of treatment. When a compound of Formula (I), (Ia), (II), and (IIa) or pharmaceutically acceptable salt thereof or a hydrate or prodrug thereof is provided in combination with a second active agent (e.g., other antifungal and/or antibacterial agents useful for treating fungal and/or bacterial infections), "administration" and its variants are each understood to include concurrent and sequential provision of the compound (or the salt, hydrate, or prodrug thereof) and of the other active agent.

As used herein, the term "composition" is intended to encompass a product comprising the specified ingredients, as well as any product that results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation, or experiment.

The term "enhanced antifungal activity" refers to the effect of a compound of Formula (I), (Ia), (II), or (IIa) or a pharmaceutically acceptable salt thereof or a hydrate or prodrug thereof having a greater than 4-fold reduction of the in vitro minimum inhibitory concentration ($MIC_{50}$) when tested in clinically relevant acidic conditions, such as, for example, conditions where the pH is about 4-4.5 (which is clinically relevant for vaginal infections), in comparison with the $MIC_{50}$ observed when tested at a neutral pH of about 7.

The term "effective amount" as used herein means an amount of active ingredient or pharmaceutical agent that elicits the biological or medicinal response in a tissue, system, animal, or human that is being sought by a researcher, veterinarian, medical doctor, or other clinician. In one embodiment, the "effective amount" can be a therapeutically effective amount that alleviates the symptoms of the disease or condition being treated. In another embodiment, the "effective amount" can be a prophylactically effective amount for prophylaxis of the symptoms of the disease or condition being prevented or for reducing the likelihood of occurrence. The term can also refer to an inhibition effective amount of the enfumafungin derivative sufficient to inhibit (1,3)-β-D-glucan synthase and thereby elicit the response being sought.

References to "treat," "treating," "treatment," and variants thereof, generally refer to a treatment that, after it is administered, results in resolution or improvement of one or more signs or symptoms associated with a fungal infection, or that results in eradication of the fungi responsible for an infection, or any combination of these outcomes.

For the purpose of preventing or treating a fungal infection, the compound of Formula (I), (Ia), (II), or (IIa) (optionally in the form of a salt or a hydrate) can be administered in conventional ways available for use in conjunction with pharmaceuticals.

For the purpose of preventing or treating fungal infections that occur in conditions or anatomic areas that have acidic pH, the compound of Formula (I), (Ia), (II), or (IIa) (optionally in the form of a salt or a hydrate) can be administered alone as an individual therapeutic agent or with one or more other antifungal agents (sequentially or concurrently) as a combination of therapeutic agents.

For the purpose of preventing or treating a fungal infection, the compound of Formula (I), (Ia), (II), or (IIa) (optionally in the form of a salt or a hydrate) can be administered with a pharmaceutical carrier selected on the basis of the chosen route of administration and standard pharmaceutical practice.

For example, the compounds of Formula (I), (Ia), (II), and (IIa), and pharmaceutically salts and/or hydrate forms thereof, can be administered by one or more of the following routes: orally, parenterally (including subcutaneous injections, intravenous, intramuscular, intra-lesion injection or infusion techniques), by inhalation (e.g., nasal or buccal inhalation spray, aerosols from metered dose inhalator, and dry powder inhalator), by nebulizer, ocularly, topically, transdermally, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose.

Further description of methods suitable for use in preparing pharmaceutical compositions and of ingredients suitable for use in said compositions is provided in *Remington's Pharmaceutical Sciences*, $20^{th}$ edition, edited by A. R. Gennaro, Mack Publishing Co., 2000.

The compounds of Formula (I), (Ia), (II), and (IIa), and pharmaceutically acceptable salts and/or hydrate forms thereof, can be administered, e.g., orally or intravenously, in a dosage range of, for example, 0.001 to 1000 mg/kg of mammal (e.g., human) body weight per day in a single dose or in divided doses. An example of a dosage range is 0.01 to 500 mg/kg body weight per day orally or intravenously in a single dose or in divided doses. Another example of a dosage range is 0.1 to 50 mg/kg body weight per day orally or intravenously in single or divided doses. For oral administration, the compositions can be provided in the form of tablets or capsules containing, for example, 1.0 to 1000 milligrams of the active ingredient, particularly 1, 5, 10, 15, 20, 25, 50, 75, 100, 150, 200, 250, 300, 400, 500, 600, 750, and 1000 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. For example, in embodiments, a pharmaceutically acceptable salt of the compound of Formula (IIa) is administered to a subject to provide a total daily dose of 150 to 600 mg of the compound of Formula (IIa). In certain embodiments, a total daily dose of 150 mg, a total daily dose of 300 mg, or a total daily dose of 600 mg of the compound of Formula (IIa) is administered; the total daily dose may be administered on a once-daily basis or it may be divided such as for BID (twice daily) dosing or TID (thrice daily) dosing. In embodiments, a pharmaceutically acceptable salt of the compound of Formula (IIa) is administered BID to provide 150 to 300 mg of the compound of Formula (IIa) twice daily, for a total daily dose of 300 mg to 600 mg of the compound of Formula (IIa). In an embodiment, two tablets containing a pharmaceutically acceptable salt of the compound of Formula (IIa), each tablet providing 150 mg of the compound of Formula (IIa), are administered to a subject, and then two more such tablets are administered to the subject 12 hours later, for a total daily dose of 600 mg. In another embodiment, a tablet containing a pharmaceutically acceptable salt of the compound of Formula (IIa), providing 150 mg of the compound of Formula (IIa), is administered to a subject, and then another such tablet is administered to the subject 12 hours later, for a total daily dose of 300 mg.

The present invention provides methods for treating or preventing a fungal infection that occurs in low pH environments (e.g., where the pH is lower than about 5), comprising administering an effective amount of a compound of Formula (I), (Ia), (II), or (IIa) (or a pharmaceutically acceptable salt or hydrate thereof), wherein the effective amount is less than the amount of the compound that would be required to treat or prevent a fungal infection occurring where the pH is about 7.

For example, the amount of a compound of Formula (I), (Ia), (II), or (IIa) effective to treat or prevent a fungal infection under pH conditions where the pH is, for example, about 4-4.5, may be about 90%, about 80%, about 70%, about 60%, or about 50% lower than the amount of the compound required to treat or prevent a fungal infection under conditions where the pH is, for example, about 7. As shown herein, in an exemplary embodiment of the methods of the present invention, the compound of Formula (I), (Ia), (II), or (IIa) or a pharmaceutically acceptable salt of hydrate thereof exhibited increased potency in low pH environments, including in environments where the pH is 4.5. In addition, good absorption and delivery to tissues (including vaginal tissues) following oral administration was exhibited in mice. The present invention therefore provides the ability to use reduced dosage amounts of a compound of Formula (I), (Ia), (II), or (IIa) (or a pharmaceutically acceptable salt or hydrate thereof) to achieve an effective amount of the compound at the site of infection.

Antifungal activity of compounds can be demonstrated by various assays known in the art, for example, by their minimum inhibitory concentration (MIC) against yeasts and minimum effective concentration (MEC) against filamentous molds and dermatophytes in a broth microdilution assay, or in vivo evaluation of the anti-*Candida* and anti *Aspergillus* activity in mouse or rabbit models. The compounds of Formula (I) provided in the Examples of U.S. Pat. No. 8,188,085 were generally found to inhibit the growth of *Candida* spp. in the range of <0.03-32 µg/mL or to give an MEC against *Aspergillus fumigatus* in the range of <0.03-32 µg/mL.

EXAMPLES

The following examples serve only to illustrate the invention and its practice. The examples are not to be construed as limitations on the scope or spirit of the invention.

Example 1

Evaluation of the Effect of pH on the Susceptibility of Clinical Vaginal *Candida Glabrata* and *Candida Albicans* Isolates The purpose of this study was to determine whether changes in test medium pH had an effect on the in vitro susceptibility of *Candida glabrata* and *Candida albicans* vaginal isolates to a representative compound of the enfumafungin derivatives (for example, the citrate salt of SCY-078), using fluconazole and micafungin as comparators.

Materials and Methods

Clinical Isolates and Antifungals

Ten strains each of *C. glabrata* and *C. albicans* vaginal isolates were tested. The strains were obtained from recent clinical trial patients with vulvovaginal candidiasis (VVC) prior to treatment. *Candida* strains were obtained from the Mycology Reference Library (MRL) at Case Western Reserve University School of Medicine, Ohio, United States.

Antifungal Susceptibility Testing

Susceptibility testing was performed using a broth microdilution method, according to CLSI M27-A3 guidelines (CLSI. 2008. Reference Method for Broth Dilution Antifungal Susceptibility Testing of Yeasts; Approved Standard—Third Edition. Clinical and Laboratory Standards Institute, CLSI document M27-A3). Antifungals and concentrations tested were SCY-078 and micafungin (both at concentrations within the range of 0.015 to 8 µg/ml) and fluconazole (at concentrations within the range of 0.125 to 64 µg/ml). A 0.1-ml *C. albicans* and *C. glabrata* inoculum of $0.5$-$2.5 \times 10^3$ blastospores/ml in RPMI 1640 medium was added to each microdilution well. ATCC strains of *Candida parapsilosis* and *Candida krusei* QC isolates were also included concurrently to ensure quality control. Antifungal susceptibility testing was carried out for each isolate in RPMI 1640 at pH 7 (to mimic RPMI medium used in testing the susceptibility of yeast by the CLSI M-27A3 document), pH 5.7, and pH 4.5 (to mimic the pH of the vaginal cavity) by adjusting the pH of the media using NaOH or HCl. Buffering of the media was achieved with morpholinepropanesulfonic acid (MOPS; 0.165 M) as described by Marr et al., *The trailing end point phenotype in antifungal susceptibility testing is PH dependent*, Antimicrob. Agents Chemother., 43: 1383-1386 (1999).

Inhibition endpoints were read as a 50% reduction in growth, as determined by optical density, compared to the growth of the control after 24 hours incubation at 35° C. SCY-078 powder was manufactured by Avista, Laboratories, NC. Micafungin and fluconazole were sourced from LGM Pharma.

Results

Activity of SCY-078 Against *C. Glabrata*

Tables 1a-1c show the MIC ranges and $MIC_{50}$ and $MIC_{90}$ for the test compounds against *C. glabrata*. The MIC ranges for SCY-078 at pH 7.0, pH 5.72 and pH 4.5 against the *C.* glabrata isolates were 0.5-1 µg/mL, 0.5 µg/mL, and 0.031-0.063 µg/mL, respectively. The $MIC_{50}$ and $MIC_{90}$ for SCY-078 at a pH of 7.0 were 1 µg/mL. The $MIC_{50}$ and $MIC_{90}$ for SCY-078 at a pH of 5.72 were 0.5 µg/mL. The $MIC_{50}$ and $MIC_{90}$ for SCY-078 at a pH of 4.5 were 0.063 µg/mL. These results showed a significant, 16-fold reduction in $MIC_{50}$ at pH 4.5 compared to the $MIC_{50}$ at pH 7.0, indicating a significant increase in antifungal potency at pH 4.5 against *Candida glabrata*.

Activity of SCY-078 Against *C. Albicans*

Tables 2a-2c show the MIC ranges and $MIC_{50}$ and $MIC_{90}$ for the test compounds against *C. albicans*. The MIC ranges for SCY-078 at pH 7.0, pH 5.72 and pH 4.5 against the *C. albicans* isolates were 0.125-0.5 µg/mL, 0.125-0.25 µg/mL, and <0.016-0.031 µg/mL, respectively. The $MIC_{50}$ for SCY-078 at pH of 7.0 and pH of 5.72 were 0.25 µg/mL, and the MIC90s were 0.5 and 0.25 µg/mL, respectively. The $MIC_{50}$ and $MIC_{90}$ for SCY-078 at pH 4.5 were <0.016 µg/mL. These results showed a significant, 16-fold reduction in $MIC_{50}$ at pH 4.5 compared to the $MIC_{50}$ at pH 7.0, indicating a significant increase in antifungal potency at pH 4.5 against *Candida albicans*.

For both *C. glabrata* and *C. albicans*, lowering the pH to 4.5 resulted in significantly lower MIC values compared to neutral pH conditions (pH 7.0). This result indicated that pH had an impact on the antifungal activity of SCY-078. This trend continued at 48 hours.

Micafungin Against *C. Glabrata*

The MIC ranges for micafungin at pH 7.0, pH 5.72 and pH 4.5 against the *C. glabrata* isolates tested were 0.25-0.5 µg/mL, 0.25 µg/mL and 0.25 µg/mL, respectively. The MIC50s of *C. glabrata* of all three pH, and the MIC90s of pH 5.72 and pH 4.5 were the same (0.25 µg/mL), while the $MIC_{90}$ of micafungin at a pH of 7.0 was 0.5 µg/mL.

Micafungin Against *C. Albicans*

The MIC ranges for micafungin at pH 7.0, pH 5.72 and pH 4.5 against the *C. albicans* isolates tested were 0.25 µg/mL, 0.063-1 µg/mL and 0.25-0.5 µg/mL, respectively. The MIC50s and MIC90s of micafungin against *C. albicans* did not differ for each pH and did not differ significantly between the pH conditions (pH 7.0 $MIC_{50}$ and $MIC_{90}$=0.25 µg/mL, pH 5.72 $MIC_{50}$ and $MIC_{90}$=1 µg/mL, pH 4.5 $MIC_{50}$ and $MIC_{90}$=0.5 µg/mL).

There were no significant differences between the minimum inhibitory concentrations (MICs) for micafungin at the three different pHs for either *C. albicans* or *C. glabrata*.

Fluconazole Against *C. Glabrata*

The MIC ranges for fluconazole at pH 7.0, pH 5.72 and pH 4.5 against the *C. glabrata* isolates tested were 0.5-2 µg/mL, 2-16 µg/mL and 1-16 µg/mL, respectively. The $MIC_{50}$ of fluconazole at 7.0, 5.72 and 4.5 pHs were 1 µg/mL, 8 µg/mL and 8 µg/mL, respectively. The $MIC_{90}$ of fluconazole at 7.0, 5.72 and 4.5 pHs were 2 µg/mL, 16 µg/mL and 16 µg/mL, respectively. These results showed a significant, 8-fold increase in $MIC_{50}$ when the activity of fluconazole at pH 7 was compared to its activity at pH 4.5, indicating a significant decrease in antifungal potency at pH 4.5 against *Candida glabrata*.

Fluconazole Against *C. Albicans*

The MIC ranges for fluconazole at pH 7.0, pH 5.72 and pH 4.5 against the *C. albicans* isolates tested were <0.125-1 µg/mL, <0.125-1 µg/mL, and 0.25-8 µg/mL, respectively. The $MIC_{50}$ and $MIC_{90}$ of fluconazole at pH 7.0, pH 5.72 and pH 4.5 were 0.25 µg/mL and 0.25 µg/mL, <0.125 and 0.25 µg/mL, and 0.25 and 1 µg/mL, respectively. The MICs of fluconazole against *C. albicans* tended to increase as the pH decreased. However, the differences were not significant.

TABLE 1a

MIC data (in µg/ml) for SCY-078 and comparators against *C. glabrata* isolates at a pH of 7.0

|  | SCY-078 | Micafungin | Fluconazole |
|---|---|---|---|
| Range | 0.5-1 | 0.25-0.5 | 0.5-2 |
| $MIC_{50}$ | 1 | 0.25 | 1 |
| $MIC_{90}$ | 1 | 0.5 | 2 |

TABLE 1b

MIC data (in µg/ml) for SCY-078 and comparators against *C. glabrata* isolates at a pH of 5.72

|  | SCY-078 | Micafungin | Fluconazole |
|---|---|---|---|
| Range | 0.5 | 0.25 | 2-16 |
| $MIC_{50}$ | 0.5 | 0.25 | 8 |
| $MIC_{90}$ | 0.5 | 0.25 | 16 |

TABLE 1c

MIC data (in µg/ml) for SCY-078 and comparators against *C. glabrata* isolates at a pH of 4.5

|  | SCY-078 | Micafungin | Fluconazole |
|---|---|---|---|
| Range | 0.031-0.063 | 0.25 | 1-16 |
| $MIC_{50}$ | 0.063 | 0.25 | 8 |
| $MIC_{90}$ | 0.063 | 0.25 | 16 |

TABLE 2a

MIC data (in µg/ml) for SCY-078 and comparators against *C. albicans* isolates at a pH of 7.0

|  | SCY-078 | Micafungin | Fluconazole |
|---|---|---|---|
| Range | 0.125-0.5 | 0.25 | <0.125-1 |
| $MIC_{50}$ | 0.25 | 0.25 | 0.25 |
| $MIC_{90}$ | 0.5 | 0.25 | 0.25 |

TABLE 2b

MIC data (in µg/ml) for SCY-078 and comparators against *C. albicans* isolates at a pH of 5.72

|  | SCY-078 | Micafungin | Fluconazole |
|---|---|---|---|
| Range | 0.125-0.25 | 0.063-1 | <0.125-1 |
| $MIC_{50}$ | 0.25 | 1 | <0.125 |
| $MIC_{90}$ | 0.25 | 1 | 0.25 |

TABLE 2c

MIC data (in µg/ml) for SCY-078 and comparators against *C. albicans* isolates at a pH of 4.5

|  | SCY-078 | Micafungin | Fluconazole |
|---|---|---|---|
| Range | <0.016-0.031 | 0.25-0.5 | 0.25-8 |
| $MIC_{50}$ | <0.016 | 0.5 | 0.25 |
| $MIC_{90}$ | <0.016 | 0.5 | 1 |

TABLE 3a-d

Individual data for *Candida* isolates (all units in µg/mL) Table 3a. MIC results for SCY-078 against the *C. glabrata* isolates tested at all pHs at 24 hours

| | | MRL SCY-078 | | | | | |
|---|---|---|---|---|---|---|---|
| | | 50% | | | 100% | | |
| | | pH | | | pH | | |
| Organism | | 7.0 | 5.72 | 4.5 | 7.0 | 5.72 | 4.5 |
| C. glabrata | 32075 | 0.5 | 0.5 | 0.063 | 1 | 1 | 0.125 |
| C. glabrata | 32232 | 1 | 0.5 | 0.063 | 1 | 1 | 0.125 |
| C. glabrata | 32626 | 0.5 | 0.5 | 0.063 | 1 | 1 | 0.125 |
| C. glabrata | 32993 | 0.5 | 0.5 | 0.031 | 1 | 1 | 0.063 |
| C. glabrata | 33204 | 1 | 0.5 | 0.031 | 1 | 1 | 0.063 |
| C. glabrata | 33960 | 0.5 | 0.5 | 0.031 | 1 | 1 | 0.063 |
| C. glabrata | 33961 | 1 | 0.5 | 0.063 | 1 | 1 | 0.063 |
| C. glabrata | 34339 | 1 | 0.5 | 0.063 | 1 | 1 | 0.125 |
| C. glabrata | 34407 | 1 | 0.5 | 0.063 | 2 | 1 | 0.125 |
| C. glabrata | 34576 | 1 | 0.5 | 0.063 | 2 | 1 | 0.125 |
| RANGE | | 0.5-1 | 0.5 | 0.031-0.063 | 1-2 | 1 | 0.063-0.125 |
| MIC$_{50}$ | | 1 | 0.5 | 0.063 | 1 | 1 | 0.125 |
| MIC$_{90}$ | | 1 | 0.5 | 0.063 | 2 | 1 | 0.125 |

TABLE 3b

MIC results for comparators against the *C. glabrata* isolates tested at all pHs at 24 hours

| | | MRL | | | | | |
|---|---|---|---|---|---|---|---|
| | | Micafungin 50% | | | Fluconazole 50% | | |
| | | pH | | | pH | | |
| Organism | | 7.0 | 5.72 | 4.5 | 7.0 | 5.72 | 4.5 |
| C. glabrata | 32075 | 0.25 | 0.25 | 0.25 | 2 | 8 | 8 |
| C. glabrata | 32232 | 0.5 | 0.25 | 0.25 | 2 | 8 | 8 |
| C. glabrata | 32626 | 0.5 | 0.25 | 0.25 | 1 | 8 | 8 |
| C. glabrata | 32993 | 0.25 | 0.25 | 0.25 | 2 | 16 | 16 |
| C. glabrata | 33204 | 0.25 | 0.25 | 0.25 | 2 | 8 | 8 |
| C. glabrata | 33960 | 0.5 | 0.25 | 0.25 | 1 | 16 | 16 |
| C. glabrata | 33961 | 0.25 | 0.25 | 0.25 | 1 | 2 | 1 |
| C. glabrata | 34339 | 0.25 | 0.25 | 0.25 | 0.5 | 2 | 8 |
| C. glabrata | 34407 | 0.25 | 0.25 | 0.25 | 1 | 8 | 8 |
| C. glabrata | 34576 | 0.25 | 0.25 | 0.25 | 1 | 8 | 16 |
| RANGE | | 0.25-0.5 | 0.25 | 0.25 | 0.5-2 | 2-16 | 1-16 |
| MIC$_{50}$ | | 0.25 | 0.25 | 0.25 | 1 | 8 | 8 |
| MIC$_{90}$ | | 0.5 | 0.25 | 0.25 | 2 | 16 | 16 |

TABLE 3c

MIC results for SCY-078 against the *C. albicans* isolates tested at all pHs at 24 hours

| | | MRL SCY-078 | | | | | |
|---|---|---|---|---|---|---|---|
| | | 50% | | | 100%* | | |
| | | pH | | | | | |
| Organism | | 7.0 | 5.72 | 4.5 | 7.0 | 5.72 | 4.5 |
| C. albicans | 34366 | 0.5 | 0.25 | 0.031 | 0.5 | 0.5 | 0.031 |
| C. albicans | 34367 | 0.125 | 0.125 | <0.016 | 0.5 | 0.5 | 0.031 |
| C. albicans | 34372 | 0.25 | 0.25 | <0.016 | 0.25 | 0.25 | <0.016 |
| C. albicans | 34373 | 0.25 | 0.25 | <0.016 | 0.25 | 0.25 | <0.016 |
| C. albicans | 34374 | 0.25 | 0.125 | <0.016 | 0.25 | 0.25 | <0.016 |
| C. albicans | 34385 | 0.25 | 0.25 | <0.016 | 0.5 | 0.5 | 0.031 |
| C. albicans | 34389 | 0.125 | 0.25 | <0.016 | 0.25 | 0.25 | 0.031 |
| C. albicans | 34399 | 0.25 | 0.25 | <0.016 | 0.25 | 0.25 | 0.031 |
| C. albicans | 34408 | 0.5 | 0.25 | <0.016 | 4 | 2 | 4 |
| C. albicans | 34449 | 0.25 | 0.25 | <0.016 | 0.5 | 0.25 | 0.031 |
| RANGE | | 0.125-0.5 | 0.125-.25 | <0.016-0.031 | 0.25-4 | 0.25-2 | <0.016-4 |
| MIC$_{50}$ | | 0.25 | 0.25 | <0.016 | 0.25 | 0.25 | 0.031 |
| MIC$_{90}$ | | 0.5 | 0.25 | <0.016 | 0.5 | 0.5 | 0.031 |

TABLE 3d

MIC results for comparators against the *C. albicans* isolates tested at all pHs at 24 hours

| | | MRL | | | | | |
|---|---|---|---|---|---|---|---|
| | | Micafungin 50% | | | Fluconazole 50% | | |
| | | pH | | | | | |
| Organism | | 7.0 | 5.72 | 4.5 | 7.0 | 5.72 | 4.5 |
| C. albicans | 34366 | 0.25 | 0.5 | 0.5 | <0.125 | <0.125 | 0.25 |
| C. albicans | 34367 | 0.25 | 0.5 | 0.5 | 0.25 | 0.25 | 1 |
| C. albicans | 34372 | 0.25 | 1 | 0.5 | <0.125 | <0.125 | 0.25 |
| C. albicans | 34373 | 0.25 | 1 | 0.5 | 0.25 | <0.125 | 0.5 |
| C. albicans | 34374 | 0.25 | 1 | 0.5 | 0.25 | <0.125 | 0.25 |
| C. albicans | 34385 | 0.25 | 1 | 0.5 | <0.125 | <0.125 | 0.25 |
| C. albicans | 34389 | 0.25 | 1 | 0.5 | <0.125 | <0.125 | 0.5 |
| C. albicans | 34399 | 0.25 | 1 | 0.5 | 1 | 1 | 8 |
| C. albicans | 34408 | 0.25 | 0.063 | 0.25 | 0.25 | 0.25 | 0.25 |
| C. albicans | 34449 | 0.25 | 0.25 | 0.5 | 0.25 | <0.125 | 0.5 |
| RANGE | | 0.25 | 0.063-1 | 0.25-0.5 | <0.125-1 | <0.125-1 | 0.25-8 |
| $MIC_{50}$ | | 0.25 | 1 | 0.5 | 0.25 | <0.125 | 0.25 |
| $MIC_{90}$ | | 0.25 | 1 | 0.5 | 0.25 | 0.25 | 1 |

These data showed that the MIC of SCY-078 against *C. glabrata* and *C. albicans* decreased as the pH decreased. The MIC values for the comparators, consistent with previous reports, seemed to be unaffected by pH in the case of micafungin, or seemed to be significantly affected by the pH in the case of fluconazole, which showed an increase in MIC values as the pH decreased, especially for *C. glabrata*.

Quality control strains *C. parapsilosis* ATCC 22019 and *C. krusei* ATCC 6258 were within their ranges for fluconazole and micafungin.

The pH ranges tested in this experiment covered the most common clinical conditions in which acidic pH is associated with a fungal infection.

Example 2

Vaginal Concentrations of SCY-078 Following Oral Administration in Mice

The objective of this study was to determine the exposure of SCY-078 in vaginal tissue and secretions, and the relationship of this exposure to concentrations of SCY-078 in plasma, following oral administration of SCY-078 to mice, a recognized model for *Candida* infections.

Methods

Female CD-1 mice (n=3/time point/dose group) were given SCY-078 via oral gavage for either one, two, or eight total doses ranging from 10 to 80 mg/kg, consisting of QD (once per day) and BID (twice per day) dose regimens, with and without loading doses, as follows:
  QD (Day 1): 10, 20, 40, 80 mg/kg
  BID (Day 1): 10/5, 20/10, 40/20, 80/40 mg/kg
  BID repeat dose (Days 1-4): 10/5, 20/10 40/20, 80/40 mg/kg on Day 1; 5, 20, 20, 40 mg/kg BID on Days 2 to 4

Blood, vulvo-vaginal tissue and vaginal secretions were collected pre-dose, and at 1, 2, 4, 6, 8, 12, 18 and 24 hours post-dose, following the final dose administered per group. Samples were then processed, extracted via protein precipitation and analyzed for SCY-078 via LC MS/MS.

Results

Following oral administration, high concentrations of SCY-078 were achieved in both vaginal tissue and vaginal secretions, relative to plasma concentration.

In vaginal tissues, SCY-078 exposure was greater than dose proportional, with the $AUC_{0-24}$ (area under the curve, measured from 0 to 24 hrs) for each dosing regimen ranging from 26.7 to 171, 24.6 to 337, and 24.4 to 1798 µg*hr/g, respectively. In the repeated-dose regimen, the accumulation potential of SCY-078 in vaginal tissue increased with increasing dose, as the ratio of the concentration in vaginal tissue following the last dose, to the concentration in vaginal tissue following the first dose, ranged from 1 to 10.5-fold.

In vaginal secretions, the $AUC_{0-24}$ for each dosing regimen ranged from 1.32 to 12.3, 1.55 to 17.8, and 4.32 to 120 µg*hr/ml, respectively. In plasma, the $AUC_{0-24}$ for each dosing regimen ranged from 8.33 to 75.5, 7.47 to 101, and 7.47 to 101 µg*hr/ml, respectively. Table 4 summarizes the exposures ($AUC_{0-24}$) per dose group.

TABLE 4

| Dose (mg/kg) | Plasma (µg*hr/ml) | Vaginal Secretion (µg*hr/ml) | Vaginal Tissue (µg*hr/g) |
|---|---|---|---|
| QD | | | |
| 10 | 8.33 | 1.32 | 26.7 |
| 20 | 19.7 | 1.87 | 53.6 |
| 40 | 42.3 | 4.41 | 187 |
| 80 | 75.5 | 12.3 | 171 |
| BID | | | |
| 10/5 | 7.47 | 1.55 | 24.6 |
| 20/10 | 16.6 | 4.21 | 72.9 |
| 40/20 | 46.5 | 10.6 | 204 |
| 80/40 | 101 | 17.8 | 337 |
| BID repeat-dose | | | |
| 10/5 | 5.12 | 4.32 | 24.4 |
| 20/10 | 14.6 | 8.63 | 71.6 |
| 40/20 | 53.0 | 38.8 | 275 |
| 80/40 | 143 | 120 | 1798 |

Following oral administration to mice, SCY-078 exposure was demonstrated in vaginal tissues, vaginal secretions, and plasma. High concentrations of SCY-078 were achieved in vaginal tissues following oral administration and, with repeat-dosing, a potential to accumulate in vaginal tissue to more than 10-fold relative to plasma was demonstrated.

Example 3

SCY-078 Phase 2 Study in Moderate and Severe Vulvovaginal Candidiasis (VVC)

This study was a proof-of-concept study conducted to evaluate the safety and efficacy of two dosing regimens of oral SCY-078 (administered as the phosphate salt) in subjects presenting with moderate to severe VVC.
Methods
Key criteria for inclusion included:
1. Subjects with moderate to severe VVC, confirmed by positive potassium hydroxide (KOH) test from a vaginal secretion sample
2. Three vaginitis episodes in the past year that were either confirmed to be caused by *Candida* spp. or that responded to antifungal therapy Subjects were randomized in a 1:1:1 ratio to one of the three treatment arms: Oral SCY-078 loading dose of 1250 mg SCY-078, followed by 750 mg SCY-078 QD for 2 days or for 4 days, or Oral Fluconazole 150 mg for 1 day.

Subjects were evaluated on Day 24 (Test-of-Cure visit), Day 60, Day 90, and 120 days (end of study).

The analyses included clinical cure (all signs and symptoms present at baseline improved by at least two points (e.g., from moderate to absent or from severe to mild); after the study started, the FDA proposed that clinical cure is achieved if all signs and symptoms present at baseline are absent), mycological eradication (a negative culture for the baseline yeast pathogen), and therapeutic cure (both clinical cure and mycological eradication). Clinical cure has been proposed by the FDA as the primary endpoint for assessment of efficacy in VVC.

Ninety-six subjects were enrolled (intent-to-treat (ITT) population), and 70 subjects had cultured-confirmed *Candida* spp. infection (per protocol (PP) population).

Table 5 summarizes the results.

The rate of mycological eradication at Day 24 and Month 4 was 70% and 74% for the SCY-078 combined arms, versus 65% and 60% for the fluconazole arm. Therapeutic cure (defined as both clinical cure and mycological eradication) at the Day 24 Test-of-Cure visit was 56.3% for the SCY-078 combined arms and the fluconazole arm. There were no severe or serious adverse events in any treatment groups. A higher rate of GI adverse events (e.g., nausea, diarrhea), which events were mild to moderate in severity and transient in nature, was reported in the SCY-078 treatment arms.

The results from the per protocol (PP) population were consistent with the results from the intent-to-treat (ITT) population (patients who received at least one dose of the study medication), as shown in Table 6.

TABLE 6

| Intent-to-Treat (ITT) Population | | |
|---|---|---|
| | Combined SCY-078 (n = 64) | Fluconazole (n = 32) |
| Clinical cure* | 78.1% | 65.6% |
| Mycological eradication | 70.3% | 68.8% |
| Therapeutic cure | 56.3% | 56.3% |

*In this analysis, clinical cure was defined as resolution of signs and symptoms of infection (signs and symptoms that had a score of 2 or 1 at baseline should be 0, and signs and symptoms with a score of 3 at baseline should be 0 or 1, at the Test-of-Cure visit).

The high clinical cure rates and the reduction of recurrence rates observed in this study provided evidence of the potent anti-*Candida* effect of SCY-078 in VVC.

Example 4

An experiment is conducted to demonstrate that the enhanced activity of SCY-078 under acidic conditions allows for a reduction of the doses needed to achieve efficacy in VVC. This is a randomized, double-blind, double-dummy, active-controlled or placebo-controlled study to evaluate the efficacy of oral SCY-078 in adult female subjects 18 years and older with moderate to severe VVC. The study evaluates doses lower than doses that have

TABLE 5

| | N Rates % | | | | |
|---|---|---|---|---|---|
| | SCY-078 (3-Days) (n = 24) | SCY-078 (5-Days) (n = 26) | SCY-078 (Combined) (n = 50) | Fluconazole (n = 20) | % Δ SCY-078 (combined) vs. Fluconazole |
| Efficacy Evaluation at Day 24 (per Protocol Population) | | | | | |
| Clinical Cure | 19 79.2% | 19 73.1% | 38 76% | 13 65% | 11% |
| Clinical Cure (Updated FDA Definition) | 17 70.8% | 18 69.2% | 35 70% | 11 55% | 15% |
| Efficacy Evauation at Month 4 | | | | | |
| Recurrences Requiring Antifungal Therapy | 1 4.2% | 1 3.8% | 2 4% | 3 15% | −11% |
| Clinical Cure | 21 87.5% | 23 88.46% | 44 88% | 13 65% | 23% |
| '0' Signs and Symptoms | 19 79.1% | 21 80.7% | 40 80% | 13 65% | 15% | been shown to elicit a response in other studies, considering the surprising finding of enhanced activity of SCY-078 under low pH conditions. The following dose regimens are evaluated:

Treatment Group 1: oral SCY-078 750 mg QD on Day 1 only

Treatment Group 2: oral SCY-078 300 mg BID on Day 1 only

Treatment Group 3: oral SCY-078 450 mg BID on Day 1 only

Treatment Group 4: oral SCY-078 150 mg BID on Days 1 to 3

Treatment Group 5: oral SCY-078 300 mg BID on Days 1 to 3

SCY-078 is administered orally in a suitable oral dosage form containing 50 mg or 100 mg or 150 mg or 200 mg or 250 mg or 300 mg or 500 mg or 750 mg of the active ingredient. Suitable oral dosage forms include, for example, tablets, capsules, suspensions, powders, granules and the like.

Having approximately 30 subjects per treatment group provides an indication of the magnitude of the effect of each dose regimen. A control arm, receiving oral fluconazole at its approved dose regimen, is included.

The patients in this study are evaluated at a Baseline visit on Day 1 and at Day 10 to evaluate efficacy. Pharmacokinetic assessments are conducted to evaluate the exposure of SCY-078 achieved in vaginal tissue and in plasma at each dosing regimen.

The subjects in this study are required to meet the following inclusion criteria:
1. Subject is a female subject 18 years or older and is in good general health.
2. Subject has a diagnosis of symptomatic VVC that meets the following criteria:
    a. Moderate to severe disease, defined as a minimum composite vulvovaginal signs and symptoms score of ≥7 with at least 2 signs or symptoms having a score of 2 (moderate) or greater in the VSS Scale at Baseline.
    b. Positive microscopic examination with 10% Potassium Hydroxide (KOH) in a vaginal sample revealing yeast forms (hyphae/pseudohyphae) or budding yeasts with subsequent confirmation of positive culture for yeast.
    c. Vaginal pH≤4.5

Efficacy is determined primarily by the percentage of subjects with clinical cure (resolution of signs and symptoms) as well as mycological eradication (negative culture) at Day 10. The data is analyzed using standard statistical software such SAS® version 9.3 or later. Statistical tests are two-sided and interpreted at a 5% significance level. The study does not need to be powered for formal statistical comparisons; rather, it provides a directional indication of the efficacy of lower doses or of shorter dose regimens of SCY-078 relative to, for example, the doses and dose regimens used in Example 3. Descriptive statistics (mean, standard deviation, median, minimum, maximum, etc.) is provided for all continuous variables; frequencies and percentages are tabulated for incidence and categorical variables. All analyses are presented by treatment group.

Example 5

An experiment is conducted to demonstrate that the enhanced activity of SCY-078 under acidic conditions allows for improved efficacy in treating VVC with a topical formulation of SCY-078. The enhanced activity of SCY-078 under low pH facilitates the development of a topical formulation that is applied in the vaginal cavity and results in improved efficacy by readily achieving local concentrations higher than the MIC required to treat or prevent the yeast causing the infection. Examples of suitable topical formulations include cream, ointment, gel, suppository, vaginal tablets or foam, and the like.

The study is a randomized, double-blind, active-controlled or placebo-controlled study to evaluate the efficacy of a topical formulation of SCY-078 in adult female subjects 18 years and older with moderate to severe VVC. This study includes 2 to 5 different dose regimens of SCY-078 and a placebo or an active comparator such as topical nystatin or topical clotrimazole or topical miconazole.

SCY-078 is administered topically in a suitable formulation containing 5 mg or 10 mg or 20 mg or 25 mg or 50 mg or 75 mg or 100 mg or 150 mg of the active ingredient. The active comparator is administered at the doses approved for this intended use.

Having approximately 30 subjects per treatment group provides an indication of the magnitude of the effect of each dose regimen.

The patients in this study are evaluated at a Baseline visit on Day 1 and at Day 10 to evaluate efficacy.

The subjects in this study are required to meet the following inclusion criteria:
1. Subject is a female subject 18 years or older and is in good general health.
2. Subject has a diagnosis of symptomatic VVC that meets the following criteria:
    a. Positive microscopic examination with 10% Potassium Hydroxide (KOH) in a vaginal sample revealing yeast forms (hyphae/pseudohyphae) or budding yeasts with subsequent confirmation of positive culture for yeast.
    b. Vaginal pH≤4.5

Efficacy is determined primarily by the percentage of subjects with clinical cure (resolution of signs and symptoms) as well as mycological eradication (negative culture) at Day 10. The data is analyzed using standard statistical software such SAS® version 9.3 or later. Statistical tests are two-sided and interpreted at a 5% significance level. The study does not need to be powered for formal statistical comparisons; rather, it provides a directional indication of the efficacy of different doses or of different dose regimens of SCY-078. Descriptive statistics (mean, standard deviation, median, minimum, maximum, etc.) are provided for all continuous variables; frequencies and percentages are tabulated for incidence and categorical variables. All analyses are presented by treatment group.

Example 6

An experiment is conducted to demonstrate that the enhanced activity of SCY-078 under acidic conditions allows for efficacy in the prevention of VVC episodes in patients suffering from recurrent VVC (rVVC). There are no current therapies approved for the prevention of VVC in patients suffering from rVVC, and an antifungal agent with enhanced activity in the vaginal milieu would have the potential to be efficacious in preventing recurrent episodes of this disease by allowing more effective killing of the yeast causing the infection and preventing re-growth.

This experiment is a randomized, double-blind, placebo-controlled study to evaluate the efficacy of an oral formulation of SCY-078 in adult female subjects 18 years and older with moderate to severe VVC. This study includes 1 to 4 different dose regimens of SCY-078. The dose regimens tested include administering 1 to 3 doses of oral SCY-078 once a month for 3 or 6 months, or once a week for 3 or 6 months, to mention some.

SCY-078 is administered orally as tablets containing 50 mg or 100 mg or 150 mg or 200 mg or 250 mg or 300 mg or 500 mg or 750 mg of the active ingredient.

The subjects in this study are required to meet the following inclusion criteria:
1. Subject is a female subject 18 years or older and is in good general health.
2. Subject has a diagnosis of symptomatic recurrent VVC, defined as at least 3 episodes of VVC in the past year, that meets the following criteria:
    a. Positive microscopic examination with 10% Potassium Hydroxide (KOH) in a vaginal sample revealing yeast forms (hyphae/pseudohyphae) or budding yeasts with subsequent confirmation of positive culture for yeast.
    b. Vaginal pH≤4.5

Efficacy is determined primarily by the percentage of subjects without recurrence during the observation period. The observation period is 6 or 9 or 12 months.

Example 7

A Phase 2, Multicenter, Randomized, Double-Blind, Double-Dummy, Active-Controlled Study to Compare the Safety and Efficacy of Oral SCY-078 to Oral Fluconazole in Subjects with Acute VVC A Phase 2 study was conducted to evaluate the safety, efficacy, tolerability, and pharmacokinetics of five dose regimens of oral SCY-078 (administered as the citrate salt) compared to oral fluconazole in adult, female patients with moderate-to-severe acute VVC (defined as having a signs and symptoms (S&S) score of 7 or greater). A total of 186 intent-to-treat (ITT) patients were randomized into six different treatment arms as follows: five different dosing regimens of oral SCY-078 and one oral fluconazole treatment arm. The modified intent-to-treat (mITT) population was used for efficacy analysis and included 153 patients with culture-confirmed *Candida* spp. vaginal infection (positive microscopic examination of vaginal secretions showing yeast, vaginal pH≤4.5) at baseline. The doses of SCY-078 tested ranged from 600 mg to 1800 mg total dose administered over the duration of treatment, and the durations of treatment were 1 or 3 days:

TABLE 7

| Total Dose (mg) | Dosing Regimen | Number of patients, ITT/mITT |
|---|---|---|
| 600 mg SCY-078 | 300 mg BID for 1 day | 30/27 |
| 750 mg SCY-078 | 750 mg QD for 1 day | 32/26 |
| 900 mg SCY-078 | 450 mg BID for 1 day | 28/21 |
| 900 mg SCY-078 | 150 mg BID for 3 days | 32/29 |
| 1800 mg SCY-078 | 300 mg BID for 3 days | 32/26 |
| 150 mg Fluconazole | 150 mg QD for 1 day | 32/24 |

The primary efficacy endpoint was clinical cure, which according to current FDA guidance is defined as complete resolution (score=0) of all signs and symptoms at the Day 10 Test-of-Cure visit without the need of additional antifungal therapy. Secondary endpoints included mycological eradication (negative culture) and a composite endpoint including both clinical cure and mycological eradication. Response was also evaluated based on the percent of patients achieving a noticeable improvement in their signs and symptoms, either by achieving an S&S score of 0 or 1 or an absolute change (reduction) in mean composite S&S score from baseline. An S&S score is based on a patient's reported symptoms (burning, itching, and irritation) and investigator-assessed signs (swelling, redness, and excoriations); each sign and symptom can be absent, mild, moderate, or severe, with a corresponding score from 0 to 3; the total composite scale is 0 to 18 points. Response was further evaluated by assessing the number of patients who received rescue antifungal therapy. Patients were assessed at the Day 10 Test-of-Cure visit and also at a Day 25 Follow-Up visit. The study was not designed to achieve statistically significant differences in any of the evaluated endpoints.

All dosage regimens of SCY-078 that were tested achieved meaningful clinical cure and mycological eradication rates. In particular, administration of a total dose of 600 mg SCY-078, given on a BID schedule (300 mg administered twice daily) for 1 day, provided optimal clinical and mycological activity and favorable tolerability. Estimated exposure with this 300 mg BID for 1 day dosing regimen is $AUC_{0-24}$ in a range from about 3 to about 8 µM*hr, and $C_{max}$ in a range of about 200 to about 500 nM.

At the Day 10 Test-of-Cure visit, patients receiving the 300 mg BID for 1 day dosing regimen (600 mg total dose) for SCY-078 showed clinical and mycological response rates in-line with the response rates of subjects in the reference fluconazole arm. Specifically, clinical cure was reported in 14 of 27 patients (52%) in the 600 mg SCY-078 dose arm, and in 14 of 24 of patients (58%) in the fluconazole arm. The percentage of patients showing an S&S score of 0 or 1 was also comparable, with 70% and 71% patients reporting this improvement in the 600 mg SCY-078 dose and fluconazole arms, respectively. The mean S&S score at this timepoint was 1.0 in the SCY-078 600 mg dose arm, versus 1.8 in the fluconazole arm. The mycological eradication at this timepoint was 63% for both arms.

At the Day 25 Follow-Up visit, the 600 mg SCY-078 dose arm showed a trend toward improved clinical and mycological outcomes when compared with the fluconazole arm. If patients continued to have signs and symptoms of VVC at the Test-of-Cure visit or later, rescue antifungal medication could be prescribed. Seven of the 24 patients treated with fluconazole (29%) received rescue antifungal medication, whereas only one of the 27 patients treated with 600 mg SCY-078 (4%) received rescue antifungal medication. In addition, the percentage of patients with clinical cure (complete resolution of signs and symptoms) at the Follow-Up visit was 70% for the SCY-078 600 mg dose arm, versus 50% for the fluconazole arm. A similar difference was observed with the 0-or-1 S&S score analysis, with 81% of patients who received 600 mg SCY-078 achieving this improvement, versus 58% of patients in the fluconazole arm. Further, the mean S&S score at Day 25 was 0.4 in the 600 mg SCY-078 dose arm, versus 2.6 in the fluconazole arm, and for this endpoint the two treatments resulted in a statistically significant difference (p=0.1). Moreover, at Day 25, mycological eradication was achieved in 48% of patients in the SCY-078 600 mg dose arm, compared to 38% of patients in the fluconazole arm.

The oral SCY-078 600 mg dose was generally well-tolerated, with self-limiting (generally one-day duration), mild-to-moderate gastrointestinal adverse events being the most commonly reported.

While this invention has been particularly shown and described with references to preferred embodiments thereof, it will be understood in light of the present disclosure by those skilled in the art that various changes in form and details may be made therein without departing from the scope of the invention encompassed by the appended claims.

What is claimed is:

1. A method of treating vulvovaginal candidiasis (VVC) infection in a subject, the method comprising administering to the subject a compound of Formula (IIa):

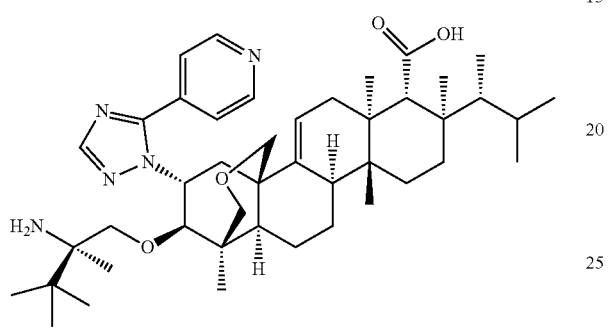

(IIa)

which is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid,
or a pharmaceutically acceptable salt or hydrate thereof,
wherein the compound or the pharmaceutically acceptable salt thereof is administered at a total daily dose of 150 to 600 mg of the compound, and
wherein the VVC infection occurs in a condition or an anatomic area in which the pH is lower than about 5.

2. The method according to claim 1, wherein the compound or the pharmaceutically acceptable salt thereof is administered at a total daily dose of 300 to 600 mg of the compound.

3. The method according to claim 1, wherein the compound or the pharmaceutically acceptable salt thereof is administered BID (twice daily) each time at a dose of 150 to 300 mg of the compound, for a total daily dose of 300 mg to 600 mg of the compound.

4. The method according to claim 1, wherein the compound or the pharmaceutically acceptable salt thereof is administered at a total daily dose of 150 mg, a total daily dose of 300 mg, or a total daily dose of 600 mg of the compound.

5. The method according to claim 1, wherein the compound or the pharmaceutically acceptable salt thereof is administered at a total daily dose of 600 mg of the compound.

6. The method according to claim 1, wherein the citrate salt of the compound of Formula (IIa) is administered.

7. The method according to claim 1, wherein the compound or the pharmaceutically acceptable salt thereof is administered orally.

8. The method according to claim 1, wherein the compound or the pharmaceutically acceptable salt thereof is administered orally in a tablet.

9. The method according to claim 1, wherein the compound or the pharmaceutically acceptable salt thereof is administered topically.

10. A method of preventing vulvovaginal candidiasis (VVC) infection in a subject, the method comprising administering to the subject a compound of Formula (IIa):

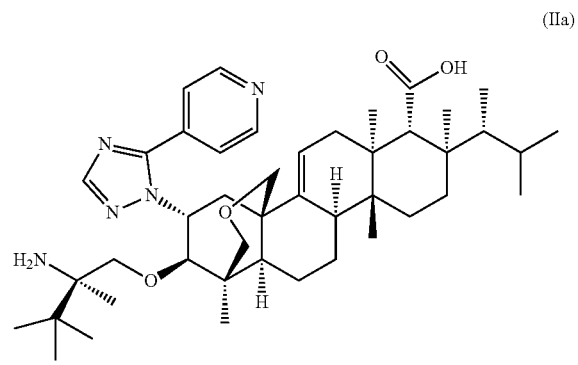

(IIa)

which is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid,
or a pharmaceutically acceptable salt or hydrate thereof,
wherein the compound or the pharmaceutically acceptable salt thereof is administered at a total daily dose of 150 to 600 mg of the compound, and
wherein the VVC infection occurs in a condition or an anatomic area in which the pH is lower than about 5.

11. The method according to claim 10, wherein the citrate salt of the compound of Formula (IIa) is administered.

12. The method according to claim 10, wherein the compound or the pharmaceutically acceptable salt thereof is administered orally.

13. The method according to claim 10, wherein the VVC infection is a recurrent VVC infection.

14. A method of treating vulvovaginal candidiasis (VVC) infection in a subject, the method comprising orally administering to the subject a citrate salt of a compound of Formula (IIa):

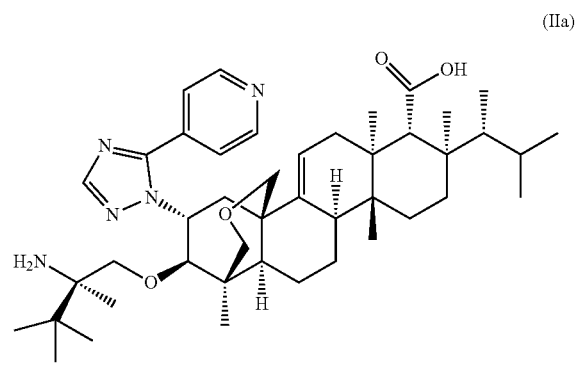

(IIa)

which is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-

1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, wherein the citrate salt of the compound is administered at a total daily dose of 150 to 600 mg of the compound.

15. The method according to claim 14, wherein the citrate salt of the compound is administered orally in a tablet.

* * * * *